United States Patent [19]

Martin

[11] Patent Number: 4,462,403
[45] Date of Patent: Jul. 31, 1984

[54] SINGLE ACTION FORCEPS FOR BONE SURGERY

[75] Inventor: Werner Martin, Rietheim, Fed. Rep. of Germany

[73] Assignee: Vernitron Corporation, Lake Success, N.Y.

[21] Appl. No.: 459,839

[22] Filed: Jan. 21, 1983

[51] Int. Cl.³ .............................................. A61B 17/16
[52] U.S. Cl. ...................................... 128/312; 30/190; 128/305; 81/408; 81/411
[58] Field of Search ............... 128/312, 751, 346, 325, 128/305; 81/383.5, 347–351, 408, 411, 416, 415, 302, 381, 383; 30/189–193, 251; 72/410

[56] References Cited

U.S. PATENT DOCUMENTS

| | | | |
|---|---|---|---|
| 126,384 | 5/1872 | Emery | 30/191 |
| 2,757,666 | 11/1954 | Grant | 81/302 |
| 3,126,005 | 3/1964 | Smialowski | 128/325 |
| 3,326,217 | 6/1967 | Kerr | 128/325 |
| 3,797,498 | 3/1974 | Walsh et al. | 128/325 |
| 4,198,749 | 4/1980 | Nordin | 30/192 |

OTHER PUBLICATIONS

Sklar Products Surgical Instruments, 18th Edition, 1973, pp. 128 and 132.

Primary Examiner—C. Fred Rosenbaum
Assistant Examiner—Gene B. Kartchner
Attorney, Agent, or Firm—Edward H. Loveman

[57] ABSTRACT

An instrument for holding and chipping a bond has a pair of elongated curved handles spaced apart at one end, and pivotally connected at other ends to ends of flat elongated jaws. Central portions of the jaws are pivotally connected together. Outer ends of the jaws and handles normally flare outwardly and are held by outwardly biased leaf springs secured to the handles. The handles pivot on a free floating disk disposed in slots formed in facting edges of the handles. The outer ends of the jaws are formed with interfitting teeth and recessed having side walls formed with sharp cutting edges.

6 Claims, 6 Drawing Figures

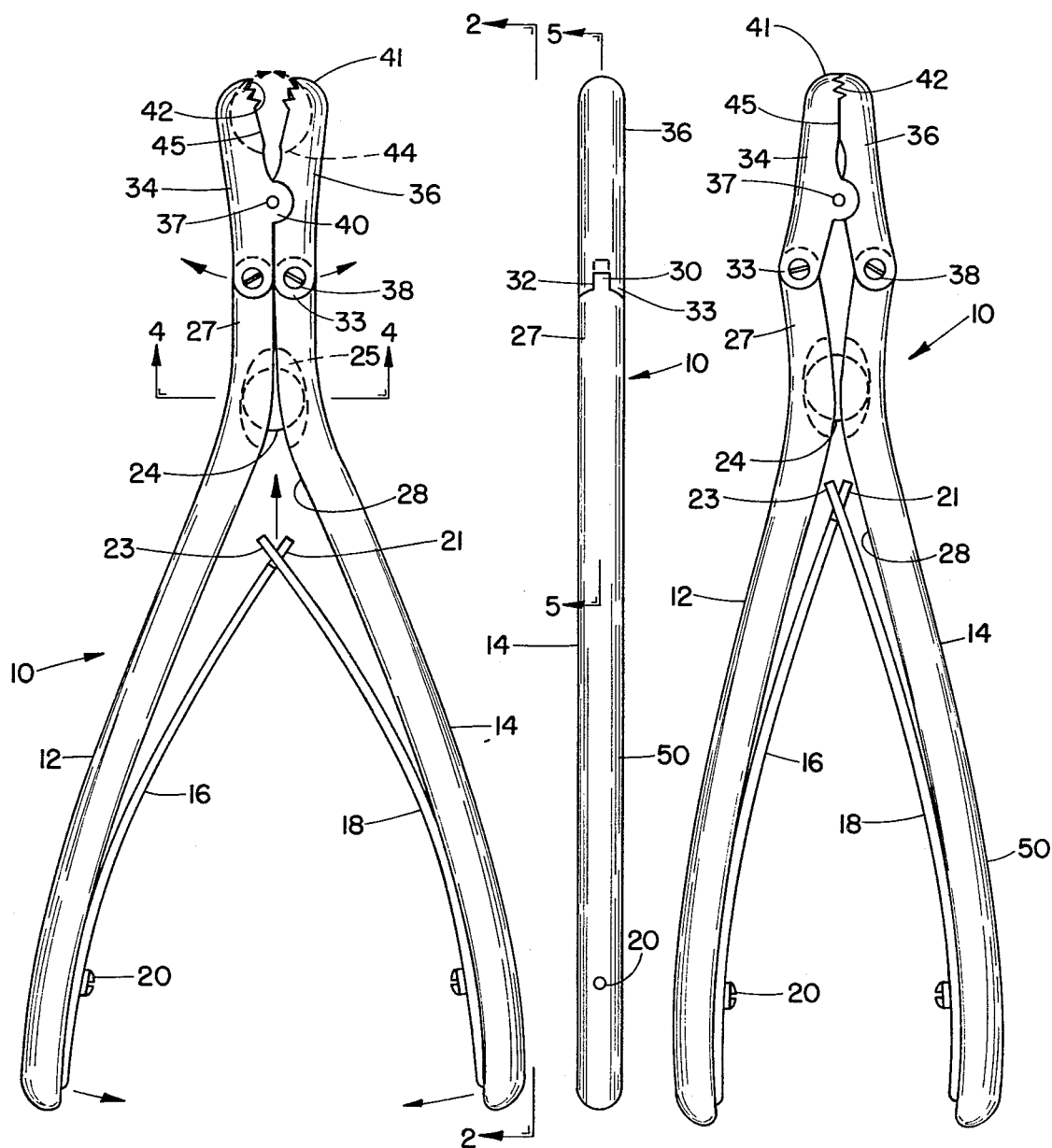

SINGLE ACTION FORCEPS FOR BONE SURGERY

This invention relates to the art of surgical instruments used in bone surgery, and more particularly concerns improved single action forceps especially useful for holding a bond firmly and for chipping a bone.

Prior forceps of the single action type employ articulated jaws having a multiplicity of pivotal joints to enable the jaws to close with increased leverage when the handles of the forceps are pressed inwardly toward each other. The joints of the prior forceps tend to wear and the jaws loosen and move laterally with respect to each other instead of coplanarly, so that perfect control of the instrument is lost. This interferes with efficient use of the instrument for grasping and chipping a bone during surgery.

The present invention is directed at providing a grasping tool such as forceps of the single action type with an improved joint structure for movable jaws. According to the invention, there is provided a free floating fulcrum disk around which the handles of the tool pivot to provide increased leverage for closing the normally open jaws of the tool. The jaws are pivotally connected to each other by one joint, and are pivotally connected to the two handles by two individual other joints. The handles are spring loaded and held separated to that the jaws are also kept separated. When the handles are manually pressed together against spring bias, their ends beyond the fulcrum disk move apart and in turn pivot the adjacent connected ends of the jaws apart. This action causes the outer free ends of the jaws to move coplanarly and come together to effect the desired grasping action.

It is therefore a principal object of the present invention to provide surgical forceps with a fulcrum disk to pivot handles of the forceps coplanarly.

A further object of the present invention is to provide forceps with two spring loaded, nonlocking handles pivoting coplanarly with respect to each other on a floating fulcrum disk enclosed by grooves in the handles.

Another object of the present invention is to provide forceps as described, with two jaws pivotally connected at one end thereof to the handles respectively, and further pivotally connected to each other, so that the normally open jaws close when the handles are pressed together against spring bias.

These and other objects and many of the attendant advantages of this invention will be readily appreciated as the same becomes better understood by reference to the following detailed description when considered in connection with the accompanying drawings in which:

FIG. 1 is a side elevational view of a surgical instrument embodying the invention, and shown in open position;

FIG. 2 is a lateral elevational view taken along line 2—2 of FIG. 1;

FIG. 3 is a side elevational view similar to FIG. 1, with the instrument shown in closed position;

Figure 5:
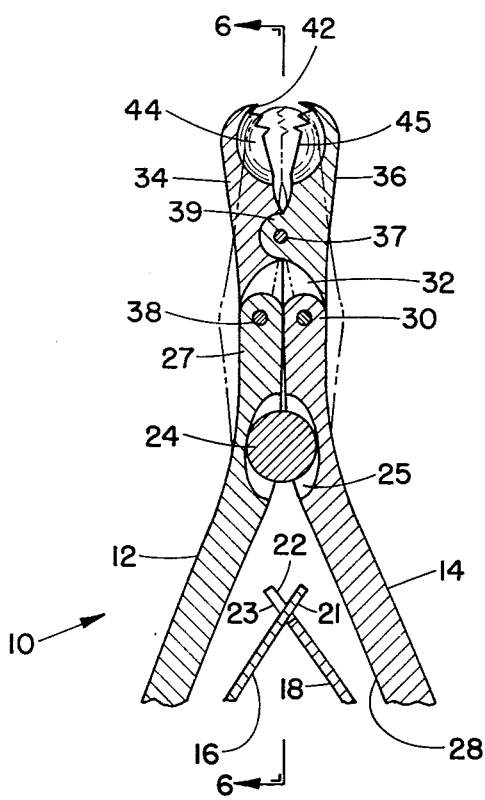
FIG. 5 is a fragmentary longitudinal sectional view taken along line 5—5 of FIG. 2.
Figure 6:
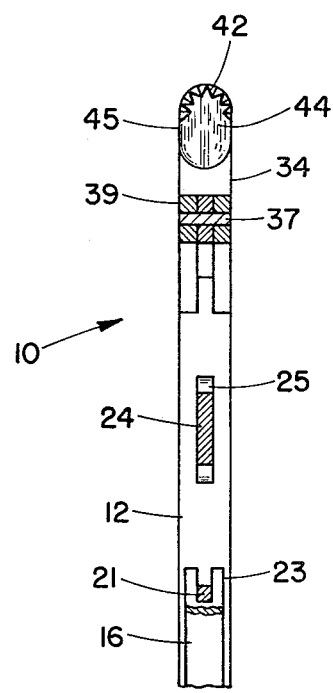
FIG. 6 is a fragmentary central sectional view taken along line 6—6 of FIG. 5.
Figure 4:
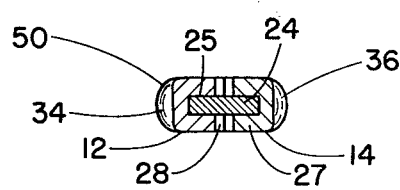
FIG. 4 is an enlarged cross sectional view taken on line 4—4 of FIG. 1.

Referring now to the drawings wherein like reference characters designate like or corresponding parts throughout, there is illustrated in FIGS. 1-6, a forceps type of tool generally designated as reference numeral 10 having two elongated handles 12, 14. At inner opposing of the handles 12, 14 are two long leaf springs 16, 18, which are secured to the handles 12, 14 by a screw 20 located near free ends of each of the handles 12, 14. The springs 16, 18, are bent and biased inwardly. At the upper end of the spring 16 is a tongue 21 engage in a slot 22 defined by a pair of spaced fingers 23 at the upper end of the spring 18. This arrangement tends to force apart the lower flared ends of the handles 12, 14. The handles 12, 14, pivot near their upper end on a disk 24 engaged at opposite edges in an elongated opposing groove 25 formed in each facing edge 28 each of the handles 12, 14. At the upper ends 27 of each of the handles 12, 14, are flanges or tenons 30 rotatably engaged in slots 32 defined by spaced flanges 33 at lower ends of jaws 34, 36. The handles 12, 14 and respective jaws 34,36, are pivotally connected together by respective pivots 38.

Jaws 34, 36 are pivotally connected together by pivot pin 37 engaged in a flange 39 rotatably fitted between spaced flanges 40 defining a slot to receive the flange 39. The interfitting flanges 39 and 40 are formed at inner edges of the jaws 34, 36. Outer free ends 41 of the jaws 34, 36, are normally spaced apart as shown in FIGS. 1 and 5. These jaws are formed with a plurality of teeth 42 which interfit as shown in FIG. 3 when the tool 10 is in closed position. Recesses 44 are formed in inner sides of the jaws 34, 36 to define a cavity when the jaws are closed. Outer edges 45 of the sides of the recesses 44 are sharp and serve as bone cutting means.

In use of the tool, the operator will grasp handles 12, 14 and squeeze them together against outward bias of springs 16, 18. The handles 12, 14, will pivot on the disk 24 acting as a flucrum causing the upper ends 27 of the handles to move apart to the position of FIG. 3. This causes the jaws 34, 36, to pivot on the pin 37 forcing the upper free ends 41 of the jaws 34, 36, together. It will be apparent that a solid bone may be grasped and held securely by the jaws 34, 36, so long as the longer, lower portions of the handles 12, 14, are squeezed toward each other. The jaws 34, 36, may cut and bite off pieces of the bone engaged between the teeth 42 and the sharp edges 45. Upon release of the handles 34, 36, the springs 16, 18, restore the tool 10 to the open position of FIGS. 1, 2, 4, 5, and 6.

It will be noted that the tool 10 has a single action, i.e. opening and closing without locking the jaws together. Release of the handles automatically opens the jaws.

All outer edges 50 of the tool are rounded and smooth, presenting no sharp protruding edges, so that the tool may be used safely in all positions. The handles of the tool are preferably made of precision ground stainless steel and the jaws of titanium steel. It is strong, durable and long lasting.

It should be understood that the foregoing relates to only a preferred embodiment of the invention, which has been by way of example only, and that it is intended to cover all changes and modifications of the examples of the invention, herein chosen for the purpose of the disclosure, which do not constitute departures from the spirit and scope of the invention.

What is claimed:

1. An instrument for holding and chipping a bone, comprising:
   a pair of flat, elongated, curved handles, arranged in coplanar disposition, and having outer free ends normally spaced widely apart and other ends normally abutted to each other;

a spring means normally holding said outer free ends of said handles spaced apart;

a pair of flat, elongated jaws having lower ends abutted to each other in coplanar disposition;

a pivot means rotatably engaging said other ends of said handles respectively to said lower ends of said jaws;

a further pivot means rotatably engaging central portions of said jaws to each other, and holding upper ends of said jaws in outwardly spaced disposition; and a free floating other pivot means serving as a fulcrum around which said handles rotate between open and closed positions of said instrument, wherein said other pivot means comprises a disk engaged in slots formed in opposing inner edges of said handles and located near said other ends thereof.

2. An instrument as defined in claim 1, wherein said upper ends of said jaws are formed with interfitting teeth and recesses having side walls formed with cutting edges to cut and chip away pieces of a bone.

3. An instrument as defined in claim 2, wherein said spring means is a pair of bent leaf springs respectively secured at lower ends thereof to said handles at said outer free ends, and having upper ends slidably and rotatably engaged together.

4. An instrument as defined in claim 3, wherein said upper end of one spring is formed with a tenon engaged in a slot formed at said upper end of the other spring.

5. An instrument as defined in claim 1, wherein said other ends of said handles are formed with tenons rotatably engaged between spaced flanges formed at said lower ends of said jaws, and held by said first named pivot means.

6. An instrument as defined in claim 5, wherein said central portion of one of said jaws is formed with another flange engaged between spaced further flanges located at said central portion of said other jaw, said further pivot means holding said other and further flanges together in rotational engagement.

* * * * *